US00PP09763P

United States Patent [19]

Utecht

[11] Patent Number: Plant 9,763

[45] Date of Patent: Dec. 24, 1996

[54] GERANIUM PLANT NAMED 'FISVIDEO'

[75] Inventor: Angelika Utecht, Montabaur, Germany

[73] Assignee: Florfis AG, Benningen, Switzerland

[21] Appl. No.: 518,895

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisvideo, characterized by its salmon semi-double flowers, early and rich flowering, dark green foliage with zonation, and compact, well branched plant habit.

1 Drawing Sheet

The present invention comprises a new and distinct cultivar of geranium, botanically known as *Pelargonium zonale*, and hereinafter referred to by the cultivar name Fisvideo.

Fisvideo is a product of a planned breeding program which had the objective of creating new geranium cultivars with salmon-pink colored semi-double flowers in combination with dark green foliage.

Fisvideo was originated from a hybridization made by the inventor Angelike Utecht in a controlled breeding program in Hillscheid, Germany, in 1991. The female parent was an unnamed hybrid seedling, characterized by salmon pink flower color and dark green foliage with only weak zonation. It was obtained by crossings between the commercial cultivars Hoennefruehling, Stadt Bern and Aphrodite. Hoennefruehling is characterized by very light pink single flowers, light green foliage with strong zonation, and compact plant habit. Stadt Bern has orange-red single flowers and dark green foliage with strong zonation. Aphrodite is a white flowering variety with light green foliage without zonation.

The male parent of Fisvideo was an unnamed seedling having orange semi-double flowers and medium green foliage with strong zonation. It was obtained by crossings between the commercial varieties Regina, Stadt Bern, Springtime Irene, and Morgengruss. Regina is characterized by light salmon and white semi-double flowers. Springtime Irene has salmon pink and white flowers, medium green zoned foliage and grows vigorously. Morgengruss is a light salmon, single flowering variety, which grows compact and starts flowering early.

Fisvideo was discovered and selected as one flowering plant within the progeny of the stated cross by Angelika Utecht in Spring 1992 in a controlled environment in Galdar, Gran Canaria, Spain. The first act of asexual reproduction of Fisvideo was accomplished when vegetative cuttings were taken from the initial selection in June 1992 in a controlled environment in Galdar, Gran Canaria, Spain, by, or under the supervision of, the inventor.

Horticultural examination of plants grown from these cuttings initiated in May, 1993 in Hillscheid, Federal Republic of Germany, and continuing thereafter, has demonstrated that the combination of characteristics as herein disclosed for Fisvideo are firmly fixed and are retained through successive generations of asexual reproduction.

Fisvideo has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisvideo, which in combination distinguish this geranium as a new and distinct cultivar:

1. Salmon flower color with a little white near margin of floret.
2. Weakly semi-double, open flower form.
3. Dark green foliage, with weak zonation.
4. Relatively compact, well branched, round plant habit.
5. Early flower response and rich flowering throughout the summer.

Of the many commercial cultiars known to the present inventor, the most similar in comparison to Fisvideo is the commercial variety Eclipse Light Salmon. Reference is made to attached Chart A which compares certain characteristics of Fisvideo to those same characteristic of Eclipse Light Salmon. In general comparison to Eclipse Light Salmon. Fisvideo has a somewhat less uniform flower color. It is intense pink near center and fades a little or turns slightly pink near margin, though there is no very broad distinct white margin. The foliage color of Fisvideo is a little lighter, while zonation is somewhat more distinct. Fisvideo starts flowering earlier and is more floriferous.

The accompanying photographic drawing shows typical flower and foliage characteristics of Fisvideo, with colors being as true as possible with illustrations of this type.

In the following description, color references are made to The Royal Horticultural Society Colour Chart. The color values were determined indoors from flowers taken from plants grown in a greenhouse in May 1994 in Hillscheid, Federal Republic of Germany.

Classification:

*Botanical.*—A hybrid of the species *Pelargonium zonale* 1Hert.

*Commercial.*—Zonal geranium, cv., Fisvideo.

Inflorescence

Umbel:

*Shape.*—Flat semi-spherical.

*Average diameter.*—110 mm.

*Average depth.*—55 mm.

*Peduncle length.*—105 mm.

*Peduncle color.*—Mainly dark red.

*Pedicel length.*—20 mm.

*Pedicel color.*—Dark red.

*Number of open flowers per umbel.*—20.

Corolla:

*Average diameter:* 40 mm.

*Form:* Semi-double.
*Number of petals:* 6–8.
*Number of petaloids:* 3.
*Color (general tonality from a distance of three meters).*—Mainly salmon, lighter or slightly pink near margin.
*Color of upper surface of petals (near center).*—43 C.
*Color of petals near margin.*—43 D–52 1 C.
*Markings of petals.*—Absent.
*Color of lower surface of petals.*—52 D–55 C.
*Color of sepals.*—Green dark red at the base.
*Number of sepals.*—5.

Bud:
*Shape.*—Broad elliptic.
*Color (adaxial).*—Green, red at the base.
*Color (abaxial).*—Light salmon pink or white.

Reproductive organs:
*Androecium.*—5–7 fertile anthers; white filaments, orange-yellow pollen.
*Gynoecium.*—5–6 lobed stigma, purple-pink style and stigma.
*Seed.*—No seed set observed.

Spring flowering response period: In Hillscheid, Federal Republic of Germany, in 1994 plants of Fisvideo had on average 1.3 umbels with at least one flower opened 11 weeks after planting of unrooted cuttings.

Outdoor flower production: The flower count in 1994 in Hillscheid, Federal Republic of Germany indicated about 45 and 50 umbels per plant for May through August observation period.

Durability: Good shatter resistance.

Plant

Foliage:
*Form.*—Kidney-shaped.
*Margin.*—Bicrenated.
*Size of leaf.*—85 mm.
*Color of upper surface.*—Dark green, approximately 137 A.
*Color of zonation.*—Brown, about 166 A.
*Tolerance of botrytis.*—Average.

General appearance and Form:
*Internode length.*—5–10 mm.
*Branching pattern.*—1.6 branches per week.
*Height of foliage.*—25 cm (in June, 16-week old plants).

Ploidy: Tetraploid.

CHART A

| | FISVIDEO | ECLIPSE LIGHT SALMON |
|---|---|---|
| Color of foliage | 137 A | 137 A–147 A |
| Zonation | Weak to medium | Weak |
| Peduncle, length | 10.5 cm | 15.5 cm |
| Number of flowers (1994) | 47 | 20 |

I claim:

1. A new distinct cultivar of geranium plant named Fisvideo, as illustrated and described.

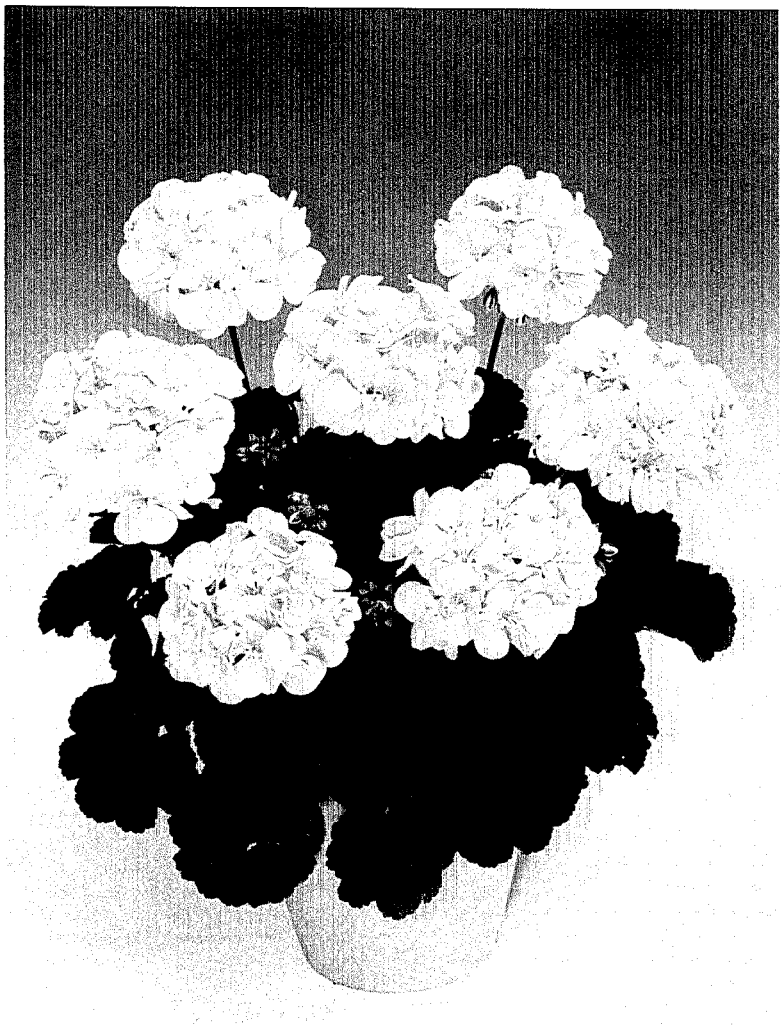

* * * * *